United States Patent [19]
Vandenberk et al.

[11] 4,254,127

[45] Mar. 3, 1981

[54] 1,3-DIHYDRO-1-[(1-PIPERIDINYL)ALKYL]-2H-BENZIMIDAZOL-2-ONE DERIVATIVES

[75] Inventors: Jan Vandenberk, Beerse; Ludo E. J. Kennis, Turnhout; Albert H. M. Th. Van Heertum; Marcel J. M. C. Van der Aa, both of Vosselaar, all of Belgium

[73] Assignee: Janssen Pharmaceutica, N.V., Beerse, Belgium

[21] Appl. No.: 137,067

[22] Filed: Apr. 3, 1980

[51] Int. Cl.$^3$ .................. C07D 401/06; A61K 31/445; C07D 401/14; C07D 409/14

[52] U.S. Cl. .................................... 424/263; 424/267; 546/199

[58] Field of Search ................. 546/199; 424/263, 267

[56] References Cited

U.S. PATENT DOCUMENTS

| | | | |
|---|---|---|---|
| 4,035,369 | 7/1977 | Vandenberk et al. | 546/199 |
| 4,181,802 | 1/1980 | Kennis | 546/199 |

*Primary Examiner*—Henry R. Jiles
*Assistant Examiner*—Robert T. Bond
*Attorney, Agent, or Firm*—Geoffrey G. Dellenbaugh

[57] ABSTRACT

Novel 1,3-dihydro-1-[(1-piperidinyl)alkyl]-2H-benzimidazol-2-one derivatives which compounds are potent serotonin-antagonists and central nervous system depressants, having utility as antiemetic, neuroleptic and anti-congestive agents.

11 Claims, No Drawings

1,3-DIHYDRO-1-[(1-PIPERIDINYL)ALKYL]-2H-BENZIMIDAZOL-2-ONE DERIVATIVES

BACKGROUND OF THE INVENTION

In U.S. Pat. No. 4,035,369 there are described a number of 1-(benzazolylalkyl)piperidine derivatives, which are useful as neuroleptic agents. These compounds are substituted on the piperidine ring with a -X-phenyl radical, wherein X is a carbonyl group or a functional derivative thereof.

The compounds of the present invention differ from these prior art compounds by nature of the substituents on the piperidine ring and by their pharmacological properties.

DESCRIPTION OF THE PREFERRED EMBODIMENTS

This invention is concerned with a novel series of 1,3-dihydro-1-[(1-piperidinyl)alkyl]-2H-benzimidazol-2-one derivatives which may structurally be represented by the formula

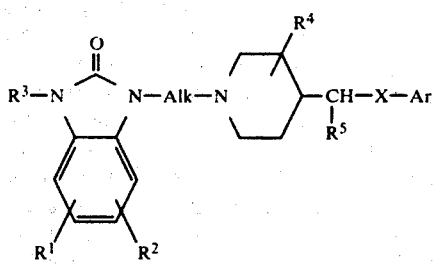

and the pharmaceutically acceptable acid addition salts thereof, wherein $R^1$ and $R^2$ are each independently selected from the group consisting of hydrogen, halo, lower alkyl and trifluoromethyl;

$R^3$ is a member selected from the group consisting of hydrogen, lower alkyl and lower alkylcarbonyl;

Alk is a lower alkylene radical;

$R^4$ and $R^5$ are each independently selected from the group consisting of hydrogen and lower alkyl;

X is a member selected from the group consisting of $>C=O$, $>CH-OH$, $>CH-O-C(O)-R_a$, $>CH_2$, $>C(O-\text{lower alkyl})_2$,

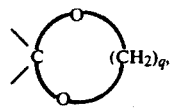

$>C=NOH$ and $>C=N-NH_2$, wherein said $R_a$ is hydrogen or lower alkyl and said q is the integer 2 or 3; and Ar is a member selected from the group consisting of phenyl, substituted phenyl, pyridinyl and thienyl, wherein said substituted phenyl has from 1 to 3 substituents each independently selected from the group consisting of halo, lower alkyl, lower alkyloxy, amino, nitro and trifluoromethyl.

As used in the foregoing definitions the term "halo" is generic to fluoro, chloro, bromo and iodo; "lower alkyl" is meant to include straight and branched hydrocarbon radicals having from 1 to 6 carbon atoms, such as, for example, methyl, ethyl, 1-methylethyl, 1,1-dimethylethyl, propyl, butyl, pentyl, hexyl and the like; and "lower alkylene", as used in the definition of Alk comprises straight and branched alkylene chains having from 1 to 4 carbon atoms.

Preferred compounds within the scope of formula (I) are those wherein $R^4$ is hydrogen. Particularly preferred compounds are those wherein $R^4$ is hydrogen and X is $>C=O$, $>C(O\text{-lower alkyl})_2$ or

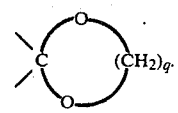

Especially preferred compounds are those wherein $R^4$ is hydrogen, X is C=O and Alk represents an 1,2-ethanediyl radical. The most preferred compound is 1-[2-[4-[2-(4-fluorophenyl)-2-oxoethyl]-1-piperidinyl]ethyl]-1,3-dihydro-2H-benzimidazol-2-one or a pharmaceutically acceptable acid addition salt thereof.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) can generally be prepared by reacting a reactive ester of formula (II) with an appropriately substituted piperidine of formula (III). In (II) and (III) $R^1$, $R^2$, $R^3$, $R^4$, $R^5$, Alk, X and Ar are as previously defined and W represents a reactive ester residue such as, for example, halo, preferably chloro, bromo or iodo, or a sulfonyloxy group, e.g., methylsulfonyloxy, 4-methylphenylsulfonyloxy and the like.

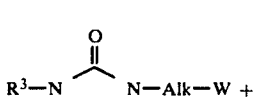

(II)

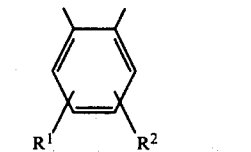

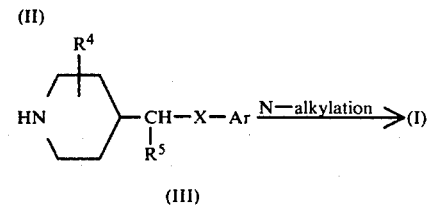

(III)

The foregoing reaction may be carried out following standard N-alkylating procedures. Said reaction is preferably carried out in an appropriate reaction-inert organic solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone; N,N-dimethylformamide; nitrobenzene; and the like. The addition of an appropriate base such as, for example, an alkali or earth alkaline metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

The compounds of formula (I) may also be prepared by reacting an appropriately substituted 1,3-dihydro-2H-benzimidazol-2-one of formula (IV) with an appropriately substituted reactive ester of formula (V), following the same N-alkylating procedure as described hereinabove for the preparation of (I) starting from (II) and (III).

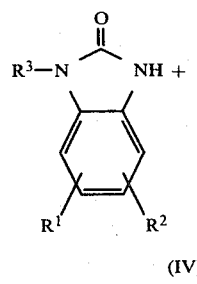

(IV)

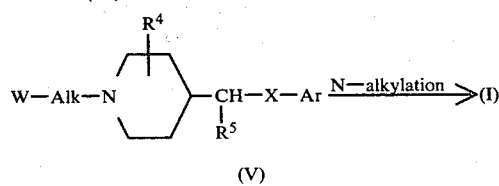

(V)

In (IV) and (V) $R^1$, $R^2$, $R^3$, $R^4$, $R^5$, X, Alk, Ar and W are as previously described.

The compounds of formula (I) can also be prepared by the reductive amination reaction of an appropriately substituted piperidine of formula (III) with an appropriate carbonyl-containing intermediate of formula (VI). $R^1$, $R^2$, $R^3$, $R^4$, $R^5$, X and Ar in the intermediates (III) and (VI) are as previously described, $Alk_1$ represents a single bond or a straight or branched lower alkylene chain having from 1 to 3 carbon atoms and $Alk_2$ represents hydrogen or a lower alkyl radical having from 1 to 3 carbon atoms, provided that the radical $-Alk_1-C(O)-Alk_2$ comprises not more than 4 carbon atoms.

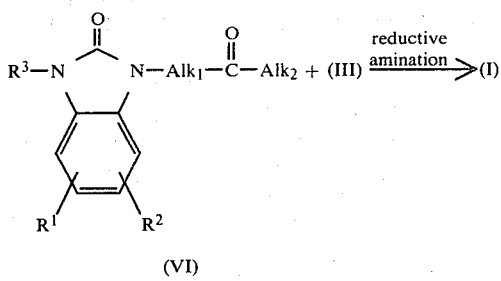

(VI)

Said reductive amination reaction may conveniently be carried out by catalytically hydrogenating a stirred and heated mixture of the reactants in a suitable reaction-inert organic solvent according to art-known catalytically hydrogenating procedures. Suitable solvents are, for example, water; lower alkanols, e.g., methanol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of 2 or more of such solvents. The term "art-known catalytically hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) wherein $R^3$ is hydrogen, said compounds being represented by the formula (I-a), can also be prepared by reacting an intermediate of formula (VII), wherein P represents an appropriate protective group, with a piperidine of formula (III) following the same procedure as previously described for the preparation of (I) starting from (II) and (III), and subsequently eliminating the protective group of the thus obtained (VIII).

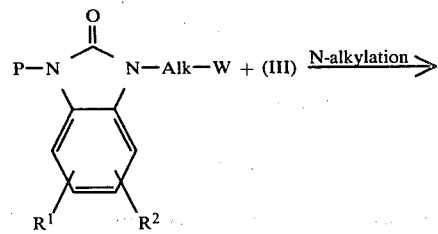

(VII)

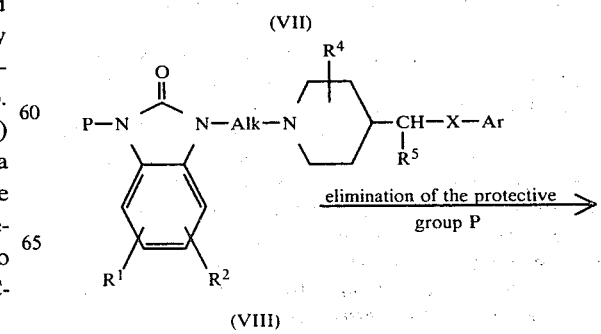

(VIII)

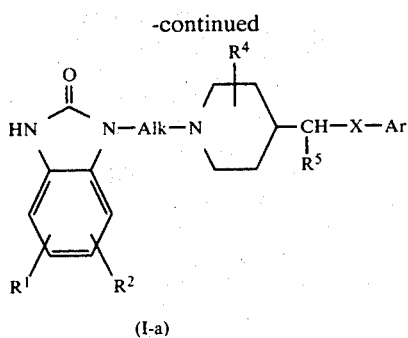

(I-a)

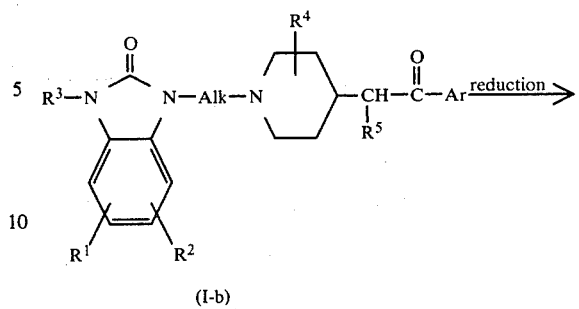

(I-b)

Appropriate protective groups are, for example, a phenylmethyl group, a lower alkyloxycarbonyl group and an optionally substituted ethenyl group. The elimination of the protective group P may be carried out following art-known procedures, depending upon the nature of P. For example, when P is a lower alkyloxycarbonyl group, P may be removed by hydrolysis in alkaline medium; when P is an optionally substituted ethenyl group it is conveniently eliminated by hydrolysis in acidic medium; when P is a benzyl radical it is easily removed by catalytic hydrogenolysis.

The compounds of formula (I) may also be prepared by cyclizing an appropriately substituted benzenediamine of formula (IX) with an appropriate cyclizing agent.

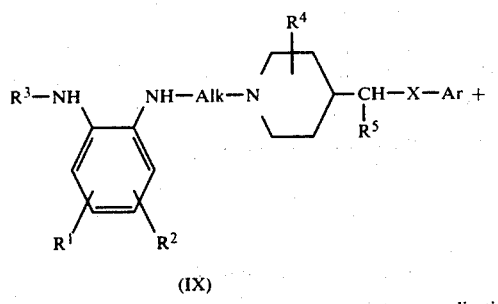

(IX)

cyclizing agent $\xrightarrow{\text{cyclization}}$ (I)

Appropriate cyclizing agents are, for example, urea, carbonyl dichloride, alkali metal cyanates, e.g., potassium cyanate, and the like. The cyclization reaction may be carried out following art-known methodologies, depending upon the nature of the cyclizing agent. For example, when urea is used, the cyclization reaction may be carried out by stirring and heating the reactants together in the absence of any solvent and, when an alkali metal salt is used, the reaction may be carried out by stirring and, if desired, heating the reactants together in the presence of an appropriate solvent, e.g., water and the like.

The compounds of formula (I) wherein X is >CO, said compounds being represented by the formula (I-b) may be converted into compounds of formula (I) wherein X is other than >CO, said compounds being represented by the formula (I-c).

The compounds of formula (I) wherein X is >CHOH, (I-c-1), may generally be prepared starting from the corresponding carbonyl compounds (I-b), by reducing the carbonyl function of the latter with an appropriate reducing agent, e.g., sodium borohydride, sodium cyanoborohydride and the like following art-known reducing procedures.

(I-c-1)

When, for example, sodium borohydride is used as a reducing agent, the reaction may conveniently be carried out in alkaline aqueous medium, if desired, in admixture with a water-miscible organic solvent such as, for example, an alicyclic ether, e.g., tetrahydrofuran, 1,4-dioxane and the like; or a lower alkanol, e.g., methanol, propanol and the like.

The compounds of formula (I) wherein X is $>CH-O-CO-R_a$, wherein $R_a$ is as previously defined, (I-c-2), may be derived from the corresponding alcohols (I-c-1) by acylating the latter with an appropriate acylating agent according to art-known procedures. Appropriate acylating agents which may be used for this purpose include lower alkanoic acids as well as acyl halides and anhydrides derived therefrom.

(I-c-1) $\xrightarrow{\text{acylation}}$

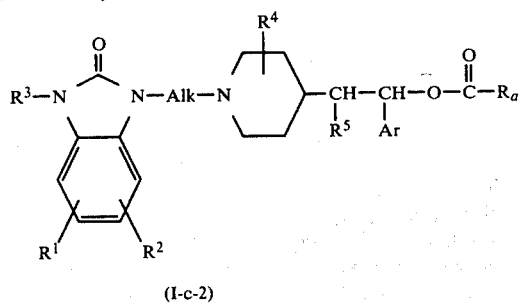

(I-c-2)

The compounds of formula (I) wherein X is a methylene radical, (I-c-3), may be derived from the corresponding carbonyl derivatives (I-b) by the reduction of the carbonyl group of (I-b) to a methylene group, e.g., by the Clemmensen reduction, using amalgated zinc and hydrochloric acid, or by the Wolff Kishner reduction, using hydrazine and alkali in a high boiling polar solvent such as, 1,2-ethanediol and the like.

(I-b) $\xrightarrow{\text{reduction}}$

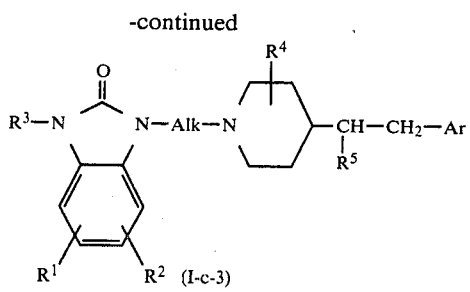

The compounds of formula (I) wherein X represents a di(lower alkyl)ketal or a cyclic lower alkylene ketal, wherein the lower alkylene chain has from 2 to 4 carbon atoms, may be derived from the corresponding carbonyl compounds by subjecting the latter to a ketalization reaction following methodologies generally known in the art. Cyclic ketals, for example, may be prepared following methodologies analogous to those described in Synthesis, 1974, (I) 23–26.

The compounds of formula (I) wherein X represents a radical of the formula >C=N—OH or a radical of the formula >C=N—NH₂ can easily be derived from the corresponding carbonyl compounds by reacting the latter with hydroxylamine hydrochloride, respectively hydrazine hydrochloride, according to art-known procedures of preparing oximes and hydrazones.

The compounds of formula (I) wherein $R^3$ is other than hydrogen, said $R^3$ being represented by $R^3_a$ and said compounds by the formula (I-d), may be prepared by reacting a compound of formula (I-a) with an appropriate acylating- or alkylating agent following art-known N-acylating- or N-alkylating procedures.

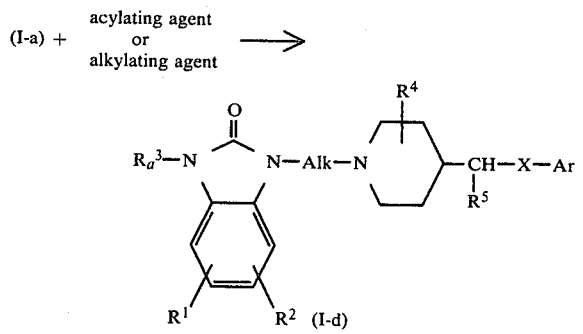

Appropriate acylating agents which may be used for this purpose include lower alkanoic acids as well as acyl halides and anhydrides derived therefrom. Appropriate alkylating agents, which may be used, include, for example, lower alkyl methanesulfonates, lower alkyl 4-methylbenzenesulfonates and the like.

Vice versa, the compounds of formula (I-a) may be derived from the compounds of formula (I-d) following art-known procedures, depending upon the nature of $R^3_a$. For example, when $R^3_a$ is lower alkylcarbonyl, (I-d) may be converted into (I-a) by hydrolyzing (I-d), preferably, in alkaline aqueous medium. When $R^3_a$ is lower alkyl, (I-d) may, for example, be converted into (I-a) by reacting (I-d) with an appropriate halogenating agent, e.g., phosphor tribromide and the like.

Certain of the intermediates and starting materials used in the foregoing preparations are known compounds, others may be prepared according to art-known methodologies of preparing similar compounds and some of them are novel and consequently their preparation will be described hereinafter.

The intermediates of formula (II) can be prepared by converting the hydroxyl function of the corresponding alcohol (X) into a reactive leaving group, e.g., by reacting the alcohol (X) with thionyl chloride, phosphor pentabromide, phosphoryl chloride, methanesulfonyl chloride, 4-methylbenzenesulfonyl chloride and the like. The alcohols (X), used as starting materials herein, can be derived from an alcohol (XI) following the same cyclizing procedure as previously described herein for the preparation of (I) starting from (IX). Alternatively, the intermediates of formula (II) can be derived from an alcohol (XI) by converting the hydroxyl function into a reactive leaving group and subsequently cyclizing the thus obtained intermediate (XII) following the previously described cyclizing procedures.

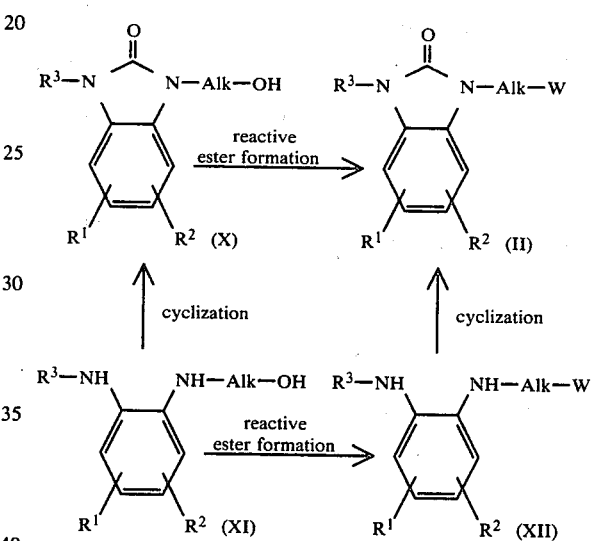

The intermediates of formula (II) can also be prepared by reacting an appropriately substituted 1,3-dihydro-2H-benzimidazol-2-one (IV) with a reagent of formula (XIII) following art-known N-alkylating procedures. In (XIII) W and W' represent both a reactive ester residue, provided that W' has a better leaving capacity than W.

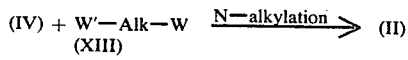

The intermediates of formula (III) wherein X is >CO, (III-a), can generally be derived from an appropriately substituted 4-piperidinone (XIV) following art-known procedures. For example, the intermediates (III) may be prepared by (i) reacting (XIV) with an appropriately substituted lower alkyl 2-cyanoacetate (XV) in a suitable solvent, e.g., water, methanol and the like, in the presence of an appropriate strong base, e.g., sodium methoxide, sodium hydroxide and the like, yielding a 1,2,3,6-tetrahydropyridine (XVI);

(ii) reducing (XVI) such as, for example, by catalytically hydrogenating (XVI) in a suitable solvent, e.g., methanol and the like, in the presence of an appropriate catalyst, e.g., palladium-on-charcoal and the like;

(iii) hydrolyzing the thus obtained (XVII) in aqueous alkaline medium and subsequently decarboxylating the intermediately formed acetic acid derivative in acidic medium, yielding a 4-piperidineacetonitrile (XVIII); and (iv) reacting said (XVIII) with an appropriate arylmagnesium halide (XIX) following art-known Grignard reaction procedure.

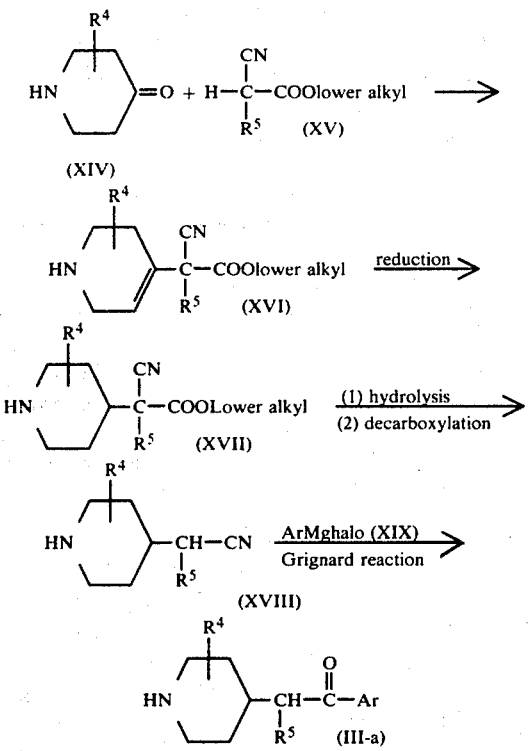

The intermediates (III) may also be prepared by reacting (XIV) with an appropriate phosphonate (XX) in a suitable organic solvent such as, for example, tetrahydrofuran, 1,2-dimethoxyethane and the like, in the presence of an appropriate base, e.g., sodium hydride and the like. This reaction is generally known as the Horner modification of the Wittig reaction. Subsequently, the thus obtained 1,2,3,6-tetrahydropyridine (XXI) is reduced, e.g., by catalytic hydrogenation in a suitable solvent, e.g., methanol, methylbenzene and the like, in the presence of an appropriate catalyst, e.g., platinum-on-charcoal and the like.

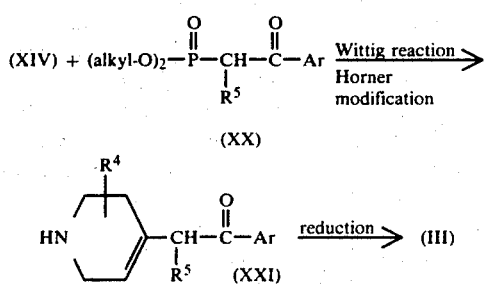

The intermediates of formula (III) can also be derived from an appropriate 4-piperidineacetic acid (XXII) by converting the latter into a corresponding acid halide (XXIII), e.g., with thionyl chloride and the like, and, subsequently, reacting said acid halide (XXIII) with an optionally substituted arene (XXIV) in the presence of a Lewis acid, e.g., aluminium trichloride and the like, following art-known Friedel Craft reaction procedures.

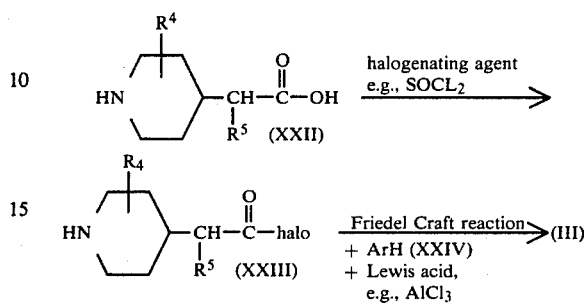

In order to enhance the yield of the conversion of (XIV) or (XXII) into (III) it may be advantageous to protect previously the piperidine-amine function with an appropriate protecting group. This protecting group can be eliminated after the conversion has been carried out. The introduction and the elimination of this protective group can be carried out following art-known procedures. Appropriate protecting groups are, for example, a phenylmethyl group, or lower alkyloxycarbonyl group and a lower alkylcarbonyl group.

The intermediates of formula (III) wherein X is other than >CO, (III-b), may be derived from the intermediates (III-a) following the same procedures as previously described for the preparations of (I-c) starting from (I-b).

The intermediates (VI) may generally be prepared by N-alkylating an appropriately substituted 1,3-dihydro-2H-benzimidazol-2-one (IV) with an appropriate ketone (XXIV) following art-known N-alkylating procedures.

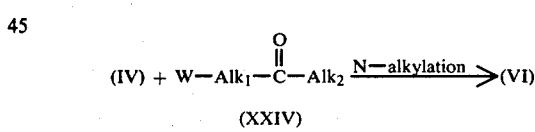

In the particular case, when $Alk_1$ is an appropriately substituted 1,2-ethanediyl radical, the intermediates (VI) may also be prepared by an 1,4-addition reaction of (IV) with an appropriately substituted vinyl ketone.

The benzenediamine (XI), wherein $R^3$ is hydrogen, (XI-a), can be prepared by reacting (XXV) with (XXVI) or (XXVII) with (XXVIII) following art-known N-alkylating procedures and subsequently reducing the thus obtained 2-nitroanilines (XXIX), e.g., by catalytic hydrogenation. The benzene diamines (XI), wherein $R^3$ is other than hydrogen, (XI-b), can be prepared by reacting (XI-a) with an appropriate alkylating or acylating agent (XXX) following art-known procedures. The reactions are shown in the following reaction-sheet.

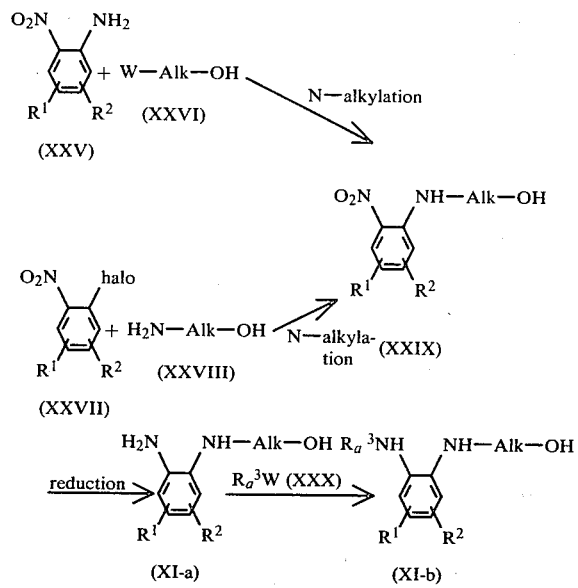

The compounds of formula (I) and the pharmaceutically acceptable acid addition salts thereof have useful pharmacological properties. They possess strong psychotropic activity and, additionally, they are very potent serotonin-antagonists and as such they can be used in the treatment of psychotropic diseases and in the treatment of a variety of compliants in which serotonin release is of predominant importance. The activity of the subject compounds as psychotropic agents is evidenced by the experimental data obtained in at least one of two different test procedures, viz., the combined apomorphine-, tryptamine- and norepinephrine tests in rats and the apomorphine test in dogs. The tests were carried out following the procedures described hereafter and the experimental data which were obtained are summarized in the table 1.

1. The combined apomorphine (APO)-, tryptamine (TRY)- and norepinephrine (NOR) test in rats.

The experimental animals used in this test were adult male Wistar rats (weight 240+10 g). After an overnight fast, the animals were treated subcutaneously (1 ml/100 g) with an aqueous solution of the compound under investigation (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena:agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures was noted. Two hours after pretreatment (time=120 minutes) finally, the same animals were challenged with 1.25 mg/kg intravenously of norephinephrine (NOR) and possible mortality was looked for up to 60 minutes later.

The table 1 gives the ED$_{50}$-values of a number of the compounds under consideration. As used herein, the ED$_{50}$-value represents the dose which protects 50% of the animals from apomorphine-, tryptamine- or norepinephrine-induced phenomena.

2. The apomorphine test in dogs (APO-dog).

The method used is described by P. A. J. Janssen and C. J. E. Niemegeers in Arzneim.-Forsch. (Drug Res), 9, 765–767 (1959).

The compounds listed in table 1 were administered subcutaneously to beagle dogs at different doses and the animals were challenged 1 hour thereafter with a standard dose of 0.31 mg/kg (subcutaneous) of apomorphine.

The table 1 gives the ED$_{50}$-values of a number of the compounds under consideration. As used herein, the ED$_{50}$-value represents the dose which protects 50% of the animals from emesis. The potency of the subject compounds as serotonin-antagonists is clearly evidenced by the results obtained in the following test wherein the antagonistic activity of the compounds (I) on the effect of serotonin is examined.

Effects in gastric lesion tests: lesions induced by compound 48/80.

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist. However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin antagonists such as, for example, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension. Table 1 shows for a number of compounds of formula (I) the doses (in mg/kg body weight) at which the distension of the stomach as well as the lesions in the glandular area of the stomach are completely absent in 50% of the test rats (ED$_{50}$-values). The compounds listed in table 1 are not given for the purpose of limiting the invention thereto but only to exemplify the useful pharmacological activities of all the compounds within the scope of formula (I).

TABLE 1

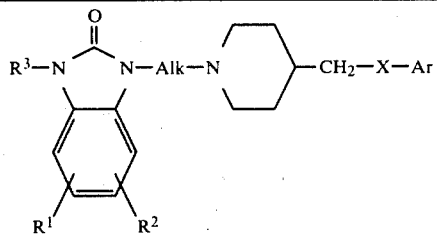

| R¹ | R² | R³ | Alk | X | Ar | base or salt | ED$_{50}$ (APO)- rat in mg/kg s.c. | ED$_0$ (TRY)- in mg/kg s.c. | ED$_{50}$ (NOR)- in mg/kg s.c. | ED$_{50}$ (APO)- dog in mg/kg s.c. | gastric lesion ED$_{50}$ in mg/kg |
|---|---|---|---|---|---|---|---|---|---|---|---|
| H | H | H | —(CH$_2$)$_3$— | CO | 4-F—C$_6$H$_4$ | base | — | 1.25 | 0.16 | — | 0.08 |
| H | H | H | —(CH$_2$)$_2$— | CO | 4-F—C$_6$H$_4$ | base | 0.31 | 0.31 | 2.5 | 0.03 | 0.01 |
| H | H | H | —(CH$_2$)$_2$—CH—<br>\|<br>CH$_3$ | CO | 4-F—C$_6$H$_4$ | base | — | 5 | 0.31 | — | 1.25 |
| 5-Cl | H | H | —(CH$_2$)$_2$— | CO | 4-F—C$_6$H$_4$ | base | 2.5 | 5 | — | 0.12 | 0.63 |
| 6-Cl | H | H | —(CH$_2$)$_2$— | CO | 4-F—C$_6$H$_4$ | base | 2.5 | 1.25 | — | 0.50 | 0.63 |
| 5-F | H | H | —(CH$_2$)$_2$— | CO | 4-F—C$_6$H$_4$ | base | 0.16 | 0.63 | 2.5 | 0.04 | 0.31 |
| 5-CH$_3$ | H | H | —(CH$_2$)$_2$— | CO | 4-F—C$_6$H$_4$ | base | 0.16 | 0.63 | 1.25 | 0.08 | 0.63 |
| H | H | CH$_3$ | —(CH$_2$)$_3$— | CO | 4-F—C$_6$H$_4$ | base | — | 1.25 | 0.31 | — | 0.31 |
| H | H | CH$_3$ | —(CH$_2$)$_2$— | CO | 4-F—C$_6$H$_4$ | base | 0.63 | 0.63 | — | 0.63 | 0.31 |
| H | H | H | —(CH$_2$)$_2$— | CO | C$_6$H$_5$ | base | 0.63 | 2.5 | 2.5 | 0.25 | 0.31 |
| H | H | H | —(CH$_2$)$_2$— | CO | 4-Cl—C$_6$H$_4$ | base | 0.63 | 2.5 | 2.5 | 0.50 | 0.16 |
| H | H | H | —(CH$_2$)$_2$— | CO | 4-CH$_3$—C$_6$H$_4$ | base | 1.25 | 2.5 | 2.5 | 0.50 | 0.63 |
| H | H | CH$_3$CO | —(CH$_2$)$_2$— | CO | 4-F—C$_6$H$_4$ | base | 1.25 | 1.25 | — | 1.0 | 0.08 |
| H | H | H | —(CH$_2$)$_3$— | CHOH | 4-F—C$_6$H$_4$ | HCl . ½H$_2$O | 2.5 | — | — | 0.50 | 0.08 |

The compounds of formula (I) completely prevent the lesions caused by excessive serotonin release and they also block the serotonin-induced contractions of bronchial tissues and of blood vessels, arteries as well as veins, and, consequently, the compounds of the present invention can be used in the treatment of gastrointestinal ulcus, bronchial spasm, hemorrhoids, varises and the like diseases, all of which are caused by congestion.

In view of their useful anti-congestive, antiemetic and psychotropic properties, the subject compounds may be formulated into various pharmaceutical forms for administration purposes. To prepare the pharmaceutical compositions of this invention, an effective anti-congestive, antiemetic and psychotropic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit from for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical anticonvulsant pharmaceutical compositions in dosage unit form suitable for systemic administration to animal and human subjects in accordance with the present invention. These examples are given to illustrate and not to limit the scope of the present invention.

Oral drops

The following formulation provides 50 liters of an oral-drop solution comprising 10 mg of 1-[2-[4-[2-(4-fluorophenyl)-2-oxoethyl]-1-piperidinyl]ethyl]-1,3-dihydro-2H-benzimidazol-2-one as the active ingredient (A.I.) per milliliter.

| A.I. | 500 grams |
|---|---|
| 2-hydroxypropanoic acid | 0.5 liters |
| sodium saccharin | 1750 grams |

-continued

| | | |
|---|---|---|
| cocoa flavor | 2.5 | liters |
| purified water | 2.5 | liters |
| polyethylene glycol q.s. ad | 50 | liters. |

The A.I. is dissolved in the 2-hydroxypropanoic acid and 1.5 liters of the polyethylene glycol at 60°–80° C. After cooling to 30°–40° C. there are added 35 liters of polyethylene glycol and the mixture is stirred well. Then there is added a solution of the sodium saccharin in 2.5 liters of purified water and while stirring there are added the cocoa flavor and polyethylene glycol q.s. ad volume. The resulting solution is filled into suitable containers.

Oral solution.

The following formulation provides 20 liters of an oral solution comprising 20 mg of 1-[2-[4-[2-(4-fluorophenyl)-2-oxoethyl]-1-piperidinyl]ethyl]-1,3-dihydro-2H-benzimidazol-2-one as the active ingredient (A.I.) per teaspoonful (5 milliliters).

| | | |
|---|---|---|
| A.I. | 20 | grams |
| 2,3-dihydroxybutanedioic acid | 10 | grams |
| sodium saccharin | 40 | grams |
| 1,2,3-propanetriol | 12 | liters |
| Sorbitol 70% solution | 3 | liters |
| Methyl 4-hydroxybenzoate | 9 | grams |
| Propyl 4-hydroxybenzoate | 1 | gram |
| Raspberry essence | 2 | milliliters |
| Gosseberry essence | 2 | milliliters |
| Purified water q.s. ad 20 liters. | | |

The methyl and propyl 4-hydroxybenzoates are dissolved in 4 liters of boiling purified water. In 3 liters of this solution are dissolved first the 2,3-dihydroxybutanedioc acid and thereafter the A.I.. The latter solution is combined with the remaining part of the former solution and the 1,2,3-propanetriol and the sorbitol solution are added thereto. The sodium saccharin is dissolved in 0.5 liters of water and the raspberry and gooseberry essences are added. The latter solution is combined with the former, water is added q.s. ad volume and the resulting solution is filled in suitable containers.

Capsules:

The following formulation provides 1000 capsules comprising each 20 mg of 1-[2-[4-[2-(4-fluorphenyl)-2-oxoethyl]-1-piperidinyl]-ethyl]-1,3-dihydro-2H-benzimidazol-2-one as the active ingredient (A.I.).

| | | |
|---|---|---|
| A.I. | 20 | grams |
| Sodium lauryl sulfate | 6 | grams |
| Starch | 56 | grams |
| Lactose | 56 | grams |
| Colloidal silicon dioxide | 0.8 | grams |
| Magnesium stearate | 1.2 | grams |

The composition is prepared by stirring the ingredients vigorously together. The resulting mixture is subsequently filled into suitable hardened gelating capsules.

CL Film-coated tablets:

10.000 compressed tablets, each containing as the active ingredient 10 mg of 1-[2-[4-[2-(4-fluorophenyl)-2-oxoethyl]-1-piperidinyl]ethyl]-1,3-dihydro-2H-benzimidazol-2-one, are prepared from the following formulation:

| | | |
|---|---|---|
| Tablet core: | | |
| A.I. | 100 | grams |
| Lactose | 570 | grams |
| Starch | 200 | grams |
| Polyvinylpyrrolidone (Kollidon-K 90) | 10 | grams |
| Microcrystalline cellulose (Avicel) | 100 | grams |
| Sodium dodecyl sulfate | 5 | grams |
| Hydrogenated vegetable oil (Sterotex) | 15 | grams |
| Coating: | | |
| Methyl cellulose (Methocel 60 HG) | 10 | grams |
| Ethyl cellulose (Ethocel 22 cps) | 5 | grams |
| 1,2,3-propanetriol | 2.5 | milliliters |
| Polyethylene glycol 6000 | 10 | grams |
| Concentrated colour suspension (Opaspray K-1-2109) | 30 | milliliters |
| Polyvinylpyrrolidone (Povidone) | 5 | grams |
| Magnesium octadecanoate | 2.5 | grams |

Preparation of tablet core:

A mixture of the A.I., the lactose and the starch is mixed well and thereafter humidified with a solution of the sodium dodecyl sulfate and the polyvinylpyrrolidone in about 200 milliliters of water. The wet powder mixture is sieved, dried and sieved again. Then there is added the microcrystalline cellulose and the hydrogenated vegetable oil. The whole is mixed well and compressed into tablets.

Coating:

To a solution of the methyl cellulose in 75 milliliters of denaturated ethanol there is added a solution of the ethyl cellulose in 150 milliliters of dichloromethane. Then there are added 75 milliliters of dichloromethane and the 1,2,3-propanetriol. The polyethylene glycol is molten and dissolved in 75 milliliters of dichloromethane. The latter solution is added to the former and then there are added the magnesium octadecanoate, the polyvinylpyrrolidone and the concentrated colour suspension and the whole is homogenated.

The tablet cores are coated with the thus obtained mixture in a coating apparatus.

Injectable solution:

The following formulation provides 1 liter of a parenteral solution comprising 4 mg of 1-[2-[4-[2-(4-fluorophenyl)-2-oxoethyl]-1-piperidinyl]ethyl]-1,3-dihydro-2H-benzimidazol-2-one as the active ingredient per milliliter.

| | | |
|---|---|---|
| A.I. | 4 | grams |
| Lactic acid | 4 | grams |
| Propylene glycol | 0.05 | grams |
| Methyl 4-hydroxybenzoate | 1.8 | grams |
| Propyl 4-hydroxybenzoate | 0.2 | grams |
| Purified water q.s. aq 1 liter. | | |

The methyl and propyl 4-hydroxybenzoates are dissolved in about 0.5 liters of boiling water for injection. After cooling to about 50° C. there are added while stirring the lactic acid, the propylene glycol and the A.I. The solution is cooled to room temperature and supplemented with water for injection q.s. ad volume. The solution is sterilized by filtration (U.S.P. XVII p. 811) and filled in sterile containers.

Suppositories:

100 Suppositories each containing 20 mg of 1-[2-[4-[2-(4-fluorophenyl)-2-oxoethyl]-1-piperidinyl]ethyl]-1,3-dihydro-2H-benzimidazol-2-one as the active ingredient are prepared from the following formulations:

| A.I. | 3 grams |
| --- | --- |
| 2,3-dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. is dissolved in a solution of the 2,3-dihydroxybutanedioic acid in the polyethylene glycol 400. The surfactant and the triglycerides are molten together. The latter mixture is mixed well with the former solution. The thus obtained mixture is poured into moulds at a temperature of 37°–38° C. to form the suppositories.

In view of the anti-congestive activity of the subject compounds, it is evident that the present invention provides a method of treating congestive diseases of warm-blooded animals by the systemic administration of an effective anti-congestive amount of a compound of formula (I) or a pharmaceutically acceptable acid addition salt thereof in admixture with a pharmaceutical carrier.

In view of the antiemetic activity of the subject compounds, it is evident that the present invention provides a method of inhibiting emesis in warm-blooded animals affected by emesis, by the systemic administration of an effective antiemetic amount of a compound of formula (I) and the pharmaceutically acceptable acid addition salts thereof in admixture with a pharamceutical carrier.

In addition, in view of the psychotropic activity of the subject compounds, the present invention also provides a method of treating mental disorders in warm-blooded animals affected by such disorders, by the systemic administration of an effective psychotropic inhibiting amount of a compound of formula (I) and the pharmaceutically acceptable acid addition salts thereof in admixture with a pharmaceutical carrier.

The following examples are intended to illustrate but not to limit the scope of the present invention. Unless otherwise stated all parts therein are by weight.

I. PREPARATION OF INTERMEDIATES.

EXAMPLE I

A mixture of 113.2 parts of 1,2,4-trichloro-5-nitrobenzene, 75 parts of 3-amino-1-propanol, 0.2 parts of potassium iodide and 200 parts of butanol is stirred and refluxed overnight. The butanol is removed by evaporation in vacuo and water is added to the residue. The product is extracted with 4-methyl-2-pentanone. The extract is washed a few times with water, dried, filtered and evaporated. The oily residue is purified by column-chromatography over silica gel using a mixture of trichloromethane and methanol (95:5 by volume) as eluent. The pure fractions are collected and the eluant is evaporated. The residue is triturated in 2,2'-oxybispropane. The product is filtered off and crystallized from a mixture of 2,2'-oxybispropane and 2-propanol, yielding 31.7 parts of 3-[(4,5-dichloro-2-nitrophenyl)amine]-1-propanol; mp. 97° C.

A mixture of 39.7 parts of 3-[(4,5-dichloro-2-nitrophenyl)amino]-1-propanol and 400 parts of methanol is hydrogenated at normal pressure and at room temperature with 5 parts of Raney-nickel catalyst. After the calculated amount of hydrogen is taken up, the catalyst is filtered off. The filtrate is acidified with 24 parts of a hydrochloric acid solution while stirring. The solvent is evaporated and the solid residue is stirred in 2-propanol. The product is filtered off and dried in vacuo, yielding 31.5 parts of 3-[(2-amino-4,5-dichlorophenyl)amino]-1-propanol hydrochloride; mp.+185° C.

To a stirred mixture of 31.2 parts of 3-[2-amino-4,5-dichlorophenyl)amino]-1-propanol hydrochloride in 200 parts of water is added dropwise, during a 15 minutes-period, a solution of 10.6 parts of potassium cyanate in 50 parts of water at a temperature between 15 and 20° C. Upon completion, stirring is continued first for 20 minutes at room temperature and further for 20 hours at reflux. The reaction mixture is allowed to cool over week-end to room temperature. The precipitated product is filtered off and boiled in trichloromethane. The undissolved part is filtered off and boiled in 4-methyl-2-pentanone. After cooling, the product is filtered off and dried, yielding 14.5 parts (48%) of 5,6-dichloro-1,3-dihydro-1-(3-hydroxypropyl)-2H-benzimidazol-2-one; mp. 174.7° C.

A mixture of 57.5 parts of 5,6-dichloro-1,3-dihydro-1-(3-hydroxypropyl)-2H-benzimidazol-2-one and 450 parts of a hydrobromic acid solution 48% in water is stirred and refluxed for 2.50 hours. The reaction mixture is cooled and water is added. The precipitated product is filtered off, stirred in 700 parts of water, filtered off again and dried in vacuo, yielding 59 parts (81%) of 1-(3-bromopropyl)-5,6-dichloro-1,3-dihydro-2H-benzimidazol-2-one; mp. 198.1° C.

EXAMPLE II

To 2 parts of a solution of 2 parts of thiophene in 40 parts of ethanol are added 71 parts of 2-[(4,5-dichloro-2-nitrophenyl)-amino]-ethanol and 400 parts of methanol. The whole is hydrogenated at normal pressure and at room temperature with 2 parts of platinum-on-charcoal catalyst 5%. After the calculated amount of hydrogen is taken up, the catalyst is filtered off and the filtrate is evaporated. The residue is taken up in methylbenzene and the latter is evaporated again. The solid residue is stirred in 2,2'-oxybispropane. The product is filtered off and dried, yielding 50 parts (81%) of 2-[(2-amino-4,5-dichlorophenyl)amino]ethanol; mp. 120° C.

A mixture of 50 parts of 2-[(2-amino-4,5-dichlorophenyl)-amino]ethanol and 46 parts of urea is stirred and heated for 2 hours in an oil-bath at about 190° C. The reaction mixture is cooled and water is added. The water is decanted and the residue is boiled in 2-propanol. Upon stirring, the mixture is cooled to room temperature. The product is filtered off and dried, yielding 55 parts (99%) of 5,6-dichloro-1,3-dihydro-1-(2-hydroxyethyl)-2H-benzimidazol-2-one.

A mixture of 55 parts of 5,6-dichloro-1,3-dihydro-1-(2-hydroxyethyl)-2-H-benzimidazol-2-one and 450 parts of a hydrobromic acid solution 48% in water is stirred and refluxed for 4 hours. The reaction mixture is poured onto ice-water and stirred to room temperature. The precipitated product is filtered off, stirred in water, filtered off again and dried, yielding 55.5 parts (87%) of 1-(2-bromoethyl)-5,6-dichloro-1,3-dihydro-2H-benzimidazol-2-one.

EXAMPLE III

A mixture of 34.8 parts of 1,3-dihydro-1-(1-methylethenyl)-2H-benzimidazol-2-one, 28 parts of 3-buten- 2-one, 20.2 parts of N,N-diethylethanamine and 270 parts of tetrahydrofuran is stirred and refluxed over week-end. The reaction mixture is evaporated, yielding 48.8 parts (100%) of 1,3-dihydro-1-(1-methylethenyl)-3-(3-oxobutyl)-2H-benzimidazol-2-one as a residue.

A mixture of 48.8 parts of 1,3-dihydro-1-(1-methylethenyl)-3-(3-oxobutyl)-2-H-benzimidazol-2-one, 12 parts of 2-propanol, saturated with gaseous hydrogen chloride and 240 parts of 2-propanol is stirred for 3 hours at room temperature. The precipitated product is filtered off, washed with 2,2'-oxybispropane and dried, yielding 30 parts (73.4%) of 1,3-dihydro-1-(3-oxobutyl)-2H-benzimidazol-2-one.

EXAMPLE IV

To a stirred mixture of 47 parts of 1,3-dihydro-1-methyl-2H-benzimidazol-2-one, 5 parts of N,N,N-triethylbenzenemethanaminium chloride and 375 parts of a sodium hydroxide solution 50% are added 96 parts of 1-bromo-3-chloropropane at 60° C. The whole is heated to 70° C. and stirring is continued for 1 hour at 70° C. The reaction mixture is poured onto crushed ice and the product is extracted with methylbenzene. The extract is washed with water, dried, filtered and evaporated, yielding 80 parts of 1-(3-chloropropyl)-1,3-dihydro-3-methyl-2H-benzimidazol-2-one as an oily residue.

EXAMPLE V

To a stirred mixture of 30 parts of 1,3-dihydro-1-(2-hydroxyethyl)-3-methyl-2H-benzimidazol-2-one and 600 parts of trichloromethane are added dropwise 200 parts of thionyl chloride. Upon completion, stirring is continued for 6 hours at reflux temperature. The reaction mixture is allowed to cool and the solvent is evaporated. The residue is crystallized from 2-propanol (activated charcoal), yielding 18.2 parts of 1-(2-chloroethyl)-1,3-dihydro-3-methyl-2H-benzimidazol-2-one.

EXAMPLE VI

A solution of 80 parts of ethyl 2-cyano-2-[1-(phenylmethyl)-4-piperidinylidene]acetate in 400 parts of methanol is hydrogenated at normal pressure and at a temperature of 30° C. in the presence of 10 parts of palladium-on-charcoal catalyst 5%. After the calculated amount of hydrogen is taken up, hydrogenation is stopped. The catalyst is filtered off and the filtrate is evaporated in vacuo. The oily residue is dissolved in water. This solution is alkalized with ammonium hydroxide and then extracted with trichloromethane. The extract is dried over magnesium sulfate and evaporated in vacuo. The oily residue is dissolved in 2,2'-oxybispropane and then gaseous hydrogen chloride is introduced into this solution. The solvent is decanted from the oily precipitate. The latter is dissolved in hot 2-propanone. After cooling to room temperature, the product crystallizes, giving after recrystallization from 2-propanol, 1 part of ethyl α-cyano-1-(phenylmethyl)-4-piperidineacetate; mp. 171.5°–172° C.

EXAMPLE VII

A mixture of 200 parts of acetic acid anhydride, 90 parts of ethyl 4-piperidineacetate and 225 parts of methylbenzene is stirred and refluxed for 3 hours. The reaction mixture is evaporated and the residue is diluted with water. The product is extracted with methylbenzene. The extract is dried, filtered and evaporated, yielding 92 parts (82%) of ethyl 1-acetyl-4-piperidineacetate as a residue.

To a stirred solution of 92 parts of ethyl 1-acetyl-4-piperidineacetate in 200 parts of ethanol are added dropwise (slowly) 65 parts of sodium hydroxide solution 30%. Upon completion, stirring is continued for 2 hours in a warm water-bath. The reaction mixture is poured onto water and the whole is filtered over hyflo. The clear filtrate is concentrated to a third of its volume and the concentrate is acidified with a diluted hydrochloric acid solution. While cooling, the product is allowed to crystallize. It is filtered off and dried, yielding 29 parts (36.5%) of 1-acetyl-4-piperidineacetic acid; mp. 124.1° C.

To 240 parts of thionyl chloride are added portionwise 25 parts of 1-acetyl-4-piperidineacetic acid and the whole is stirred overnight at room temperature. The reaction mixture is evaporated, yielding 26.5 parts (95%) of 1-acetyl-4-piperidineacetyl chloride as an oily residue.

EXAMPLE VIII

A mixture of 9.25 parts of 1-acetyl-4-piperidineacetic acid and 40 parts of thionyl chloride is stirred overnight at room temperature. The reaction mixture is evaporated in vacuo at 30°–40° C. and the residue is dissolved in 50 parts of methoxybenzene. Then there are added portionwise 13.5 parts of aluminium chloride while stirring. Upon completion, stirring is continued for 1 hour at 60° C. After cooling, the mixture is poured onto a mixture of crushed ice and hydrochloric acid and the product is extracted with dichloromethane. The extract is dried, filtered and evaporated. The residue is purified by column-chromatography over silica gel using a mixture of trichloromethane and methanol (95:5 by volume) as eluent. The pure fractions are collected and the eluent is evaporated, yielding 10 parts (73%) of 1-acetyl-4-[2-(4-methoxyphenyl)-2-oxoethyl]piperidine as a residue.

In a similar manner there are also prepared:
1-acetyl-4-[2-(4-chlorophenyl)-2-oxoethyl]piperidine as a residue; and
1-acetyl-4-[2-(4-methylphenyl)-2-oxoethyl]piperidine as a residue.

EXAMPLE IX

To a stirred mixture of 50 parts of fluorobenzene and 32 parts of aluminium trichloride is added dropwise (slowly) a solution of 26.5 parts of 1-acetyl-4-piperidineacetyl chloride in 50 parts of fluorobenzene. Upon completion, stirring is continued for 2 hours at reflux temperature. The reaction mixture is cooled to room temperature and poured onto a mixture of crushed ice and a hydrochloric acid solution. The aqueous phase is separated and extracted with methylbenzene. The combined organic phases are dried, filtered and evaporated, yielding 31 parts (90%) of 2-(1-acetyl-4-piperidinyl)-1-(4-fluorophenyl)ethanone as a residue.

In a similar manner there is also prepared:
1-acetyl-4-[2-(4-bromophenyl)-2-oxoethyl]piperidine as a residue.

EXAMPLE X

A mixture of 10 parts of 1-acetyl-4-[2-(4-methoxyphenyl)-2-oxoethyl]piperidine and 50 parts of a hydrochloric acid solution 6 N is stirred and heated for 4 hours at 100° C. The reaction mixture is allowed to cool to room temperature. The precipitated product is filtered off and crystallized from 2-propanol, yielding 5.8 parts (59%) of 1-(4-methoxyphenyl)-2-(4-piperidinyl)ethanone hydrochloride; mp. 250.7° C.

Following the same hydrolyzing procedure there are also prepared:

1-(4-fluorophenyl)-2-(4-piperidinyl)ethanone hydrochloride;

1-(4-bromophenyl)-2-(4-piperidinyl)ethanone hydrochloride; mp. 260° C.;

1-(4-chlorophenyl)-2-(4-piperidinyl)ethanone hydrochloride; mp. 263.1° C.; and 1-(4-methylphenyl)-2-(4-piperidinyl)ethanone hydrochloride.

EXAMPLE XI

A mixture of 58 parts of ethyl α-cyano-1-(phenylmethyl)-4-piperidineacetate and 125 parts of sodium hydroxide solution 2 N is stirred for 3 hours at room temperature. The mixture is neutralized with concentrated hydrochloric acid while cooling and the solvent is evaporated. The residue is stirred for 4 hours at 150° C. in 180 parts of N,N-dimethylacetamide. The reaction mixture is cooled, filtered and the filtrate is evaporated. The residue is taken up in water and extracted with methylbenzene. The extract is dried, filtered and evaporated. The residue is distilled, yielding 35 parts (82%) of 1-(phenylmethyl)-4-piperidineacetonitrile; bp. 135°–140° C. at 0.2–0.3 mm. pressure.

EXAMPLE XII

To a stirred and refluxing Grignard-complex, previously prepared starting from 3.65 parts of magnesium, 26 parts of 1-bromo-3-methylbenzene and 70 parts of 1,1'-oxybisethane, is added dropwise a solution of 21.4 parts of 1-(phenylmethyl)-4-piperidineacetonitrile in 70 parts of 1,1'-oxybisethane. Upon completion, stirring is continued for 4 hours at reflux temperature. The reaction mixture is cooled in and ice-bath and decomposed by the addition of a saturated ammonium chloride solution. The layers are separated and the aqueous phase is extracted twice with 1,1'-oxybisethane. The combined organic phases are dried, filtered and evaporated. The oily residue is purified by column-chromatography over silica gel using a mixture of trichloromethane and methanol (95:5 by volume) as eluent. The pure fractions are collected and the eluent is evaporated. The oily residue is stirred in 2,2'-oxybispropane with activated charcoal. The latter is filtered off till a clear filtrate is obtained. The filtrate is acidified with 2-propanol saturated with hydrogen chloride. The whole is evaporated and the residue is crystallized from warm 4-methyl-2-pentanone, yielding 24.5 parts (71%) of 1-(3-methylphenyl)-2-[1-(phenylmethyl)-4-piperidinyl]ethanone hydrochloride; mp. 165.8° C.

In a similar manner there are also prepared:

1-(3-chlorophenyl)-2-[1-(phenylmethyl)-4-piperidinyl]ethanone hydrochloride; mp. 168.8° C.; and 1-(3-fluorophenyl)-2-[1-(phenylmethyl)-4-piperidinyl]ethanone; mp. 54.4° C.

EXAMPLE XIII

To a stirred mixture of 20.9 parts of 1-(3-methylphenyl)-2-[1-(phenylmethyl)-4-piperidinyl]ethanone, 0.75 parts of sodium carbonate and 150 parts of trichloromethane are added dropwise 8.1 parts of ethyl chloroformate. Upon completion, stirring is continued overnight at room temperature. Water is added to the reaction mixture and the layers are separated. The aqueous phase is extracted with trichloromethane. The combined organic phases are washed with water, dried, filtered and evaporated. The residue is purified by column-chromatography over silica gel using a mixture of trichloromethane and methanol (95:5 by volume) as eluent. The pure fractions are collected and the eluent is evaporated, yielding 18 parts (91%) of ethyl 4-[2-(3-methylphenyl)-2-oxoethyl]-1-piperidinecarboxylate as an oily residue.

In a similar manner there are also prepared:

ethyl 4-[2-(3-chlorophenyl)-2-oxoethyl]-1-piperidinecarboxylate as a residue; and ethyl 4-[2-(3-fluorophenyl)-2-oxoethyl]-1-piperidinecarboxylate as an oily residue.

EXAMPLE XIV

A mixture of 19 parts of ethyl 4-[2-(3-chlorophenyl)-2-oxoethyl]-1-piperidinecarboxylate and 120 parts of a hydrobromic acid solution 48% in water is stirred and refluxed for 2 hours. The reaction mixture is evaporated and the solid residue is boiled in 2-propanol. The product is filtered off after cooling, washed with 2-propanol and dried in vacuo, yielding 17.5 parts (90%) of 1-(3-chlorophenyl)-2-(4-piperidinyl)ethanone hydrobromide; mp. 214.1° C.

In a similar manner there are also prepared:

1-(3-methylphenyl)-2-(4-piperidinyl)ethanone hydrobromide; mp. 187.7° C.; and 1-(3-fluorophenyl)-2-(4-piperidinyl)ethanone hydrobromide; mp. 221.4° C.

EXAMPLE XV

To a stirred mixture of 41 parts of diethyl [2-(3-methoxyphenyl)-2-oxoethyl]phosphonate and 180 parts of tetrahydrofuran are added portionwise 5 parts of sodium hydride dispersion 61% while cooling at about 15° C. Upon completion, stirring is continued for 30 minutes at room temperature. Then there are added dropwise 21 parts of ethyl 4-oxo-1-piperidinecarboxylate at about 20° C. Stirring is continued for 4 hours at 60° C. The reaction mixture is cooled, water is added and the layers are separated. The organic phase is dried, filtered and evaporated. The residue is distilled, yielding 30 parts (83%) of ethyl 2,3-dihydro-4-[2-(3-methoxyphenyl)-2-oxoethyl]-1(6H)-pyridinecarboxylate; bp. 200°–210° C. at 1 mm. pressure.

A mixture of 30 parts of ethyl 2,3-dihydro-4-[2-(3-methoxyphenyl)-2-oxoethyl]-1(6H)-pyridinecarboxylate, 15 parts of 1,2-ethanediol, 0.1 parts of 4-methylbenzenesulfonic acid and 135 parts of methylbenzene is stirred and refluxed overnight. The reaction mixture is cooled and evaporated, yielding 30 parts of ethyl 2,3-dihydro-4-[2-(3-methoxyphenyl)-1,3-dioxolan-2-ylmethyl]-1(6H)-pyridinecarboxylate as a residue.

A mixture of 30 parts of ethyl 2,3-dihydro-4-[2-(3-methoxyphenyl)-1,3-dioxolan-2-ylmethyl]-1(6H)-pyridinecarboxylate and 450 parts of methylbenzene is hydrogenated at normal pressure and at room temperature with 4 parts of platinum-on-charcoal catalyst 5%. After the calculated amount of hydrogen is taken up, the catalyst is filtered off and the filtrate is evaporated, yielding 30 parts of ethyl 4-[2-(3-methoxyphenyl)-1,3-dioxolan-2-ylmethyl]-1-piperidinecarboxylate as a residue.

A mixture of 30 parts of ethyl 4-[2-(3-methoxyphenyl)-1,3-dioxolan-2-ylmethyl]-1-piperidinecarboxylate, 225 parts of a hydrobromic acid solution 48% in water and a small amount of 2-propanol is stirred and refluxed for 2 hours. The reaction mixture is cooled.

The precipitated product is filtered off and dried, yielding 9.5 parts (30%) of 1-(3-methoxyphenyl)-2-(4-piperidinyl)ethanone hydrobromide.

EXAMPLE XVI

A mixture of 5.5 parts of 1-(3-chloropropyl)-1,3-dihydro-3-(1-methylethenyl)-2H-benzimidazol-2-one, 6 parts of 1-(3-methylphenyl)-2-(4-piperidinyl)ethanone hydrobromide, 8.5 parts of sodium carbonate and 120 parts of 4-methyl-2-pentanone is stirred and refluxed overnight using a water-separator. The reaction mixture is cooled, water is added and the layers are separated. The 4-methyl-2-pentanone-phase is dried, filtered and evaporated, yielding 8.6 parts (100%) of 1,3-dihydro-1-(1-methylethenyl)-3-[3-[4-[2-(3-methylphenyl)-2-oxoethyl]-1-piperidinyl]propyl]-2H-benzimidazol-2-one as an oily residue.

In a similar manner there are also prepared:

1-[3-[4-[2-(3-chlorophenyl)-2-oxoethyl]-1-piperidinyl]propyl]-1,3-dihydro-3-(1-methylethenyl)-2H-benzimidazol-2-one as a residue; and 1-[3-[4-[2-(4-bromophenyl)-2-oxoethyl]-1-piperidinyl]propyl]-1,3-dihydro-3-(1-methylethenyl)-2H-benzimidazol-2-one; as a residue.

II. PREPARATION OF FINAL COMPOUNDS:

EXAMPLE XVII

A mixture of 2.16 parts of 1-(2-chloroethyl)-1,3-dihydro-2H-benzimidazol-2-one, 2.57 parts of 1-(4-fluorophenyl)-2-(4-piperidinyl)ethanone hydrochloride, 5.3 parts of sodium carbonate, 0.2 parts of potassium iodide and 200 parts of 4-methyl-2-pentanone is stirred and refluxed for 15 hours using a water-separator. The reaction mixture is cooled, water is added and the layers are separated. The organic phase is dried, filtered and evaporated. The residue is crystallized from a mixture of 2,2′-oxybispropane and 2-propanol. The product is filtered off and dried, yielding 2.5 parts of 1-[2-[4-[2-(4-fluorophenyl)-2-oxoethyl]-1-piperidinyl]ethyl]-1,3-dihydro-2H-benzimidazol-2-one; mp. 180.6° C.

Following the same N-alkylating procedure and using equivalent amounts of the appropriate starting materials there are also prepared:

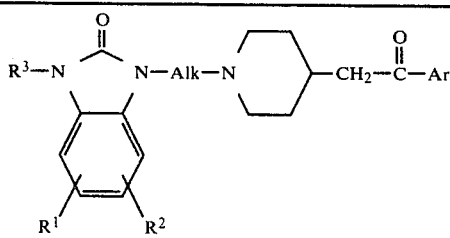

| $R^1$ | $R^2$ | $R^3$ | Alk | Ar | Base or Salt | mp.in °C. |
|---|---|---|---|---|---|---|
| 5-Cl | H | H | (CH$_2$)$_2$ | 4-F—C$_6$H$_4$ | base | 179.2 |
| 6-Cl | H | H | (CH$_2$)$_2$ | 4-F—C$_6$H$_4$ | base | 174.6 |
| 5-Cl | H | H | (CH$_2$)$_3$ | 4-F—C$_6$H$_4$ | base | 204 |
| 5-F | H | H | (CH$_2$)$_2$ | 4-F—C$_6$H$_4$ | base | 148.3 |
| 6-Cl | H | H | (CH$_2$)$_3$ | 4-F—C$_6$H$_4$ | base | 169.4 |
| 5-F | H | H | (CH$_2$)$_3$ | 4-F—C$_6$H$_4$ | base | 198.9 |
| 5-CH$_3$ | H | H | (CH$_2$)$_2$ | 4-F—C$_6$H$_4$ | base | 200.1 |
| 5-CH$_3$ | H | H | (CH$_2$)$_3$ | 4-F—C$_6$H$_4$ | base | 204.7 |
| H | H | CH$_3$ | (CH$_2$)$_3$ | 4-F—C$_6$H$_4$ | base | 90.3 |
| H | H | CH$_3$ | (CH$_2$)$_2$ | 4-F—C$_6$H$_4$ | base | 129.5 |
| H | H | H | (CH$_2$)$_2$ | C$_6$H$_5$ | base | 163.1 |
| 5-Cl | 6-Cl | H | (CH$_2$)$_2$ | 4-F—C$_6$H$_4$ | base | 179.2 |
| H | H | H | (CH$_2$)$_2$ | 4-Cl—C$_6$H$_4$ | base | 198.2 |

-continued

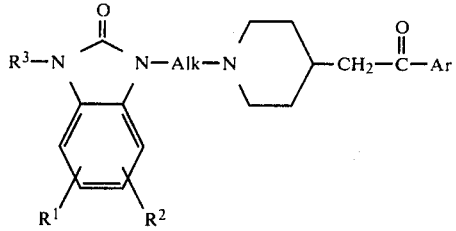

| $R^1$ | $R^2$ | $R^3$ | Alk | Ar | Base or Salt | mp.in °C. |
|---|---|---|---|---|---|---|
| H | H | H | (CH$_2$)$_2$ | 4-CH$_3$—C$_6$H$_4$ | base | 180.9 |
| H | H | H | (CH$_2$)$_3$ | 4-Cl—C$_6$H$_4$ | base | 181.3 |
| H | H | H | (CH$_2$)$_3$ | C$_6$H$_5$ | base | 162 |
| 5-Cl | 6-Cl | H | (CH$_2$)$_3$ | 4-F—C$_6$H$_4$ | base | 196.7 |
| H | H | H | (CH$_2$)$_3$ | 4-CH$_3$—C$_6$H$_4$ | base | 187.1 |
| H | H | H | (CH$_2$)$_2$ | 3-OCH$_3$—C$_6$H$_4$ | HCl | 256.3 |
| H | H | H | (CH$_2$)$_2$ | 3-Cl—C$_6$H$_4$ | base | 166.7 |
| H | H | H | (CH$_2$)$_2$ | 3-CH$_3$—C$_6$H$_4$ | base | 146.8 |
| H | H | H | (CH$_2$)$_2$ | 3-F—C$_6$H$_4$ | base | 147.6 |

EXAMPLE XVIII

A mixture of 2.3 parts of 1-(3-chloropropyl)-1,3-dihydro-2H-benzimidazol-2-one, 2.57 parts of 1-(4-fluorophenyl)-2-(4-piperidinyl)ethanone hydrochloride, 2.65 parts of sodium carbonate and 22.5 parts of N,N-dimethylformamide is stirred for 4 hours at 70°–80° C. The reaction mixture is poured onto water and the product is extracted with trichloromethane. The extract is dried, filtered and evaporated. The residue is crystallized from 4-methyl-2-pentanone. The product is filtered off and recrystallized from 2-propanol, yielding 1.4 parts (35%) of 1-[3-[4-[2-(4-fluorophenyl)-2-oxoethyl]-1-piperidinyl]propyl]-1,3-dihydro-2H-benzimidazol-2-one; mp. 208° C.

EXAMPLE XIX

A mixture of 3.92 parts of 1-(2-chloroethyl)-1,3-dihydro-2H-benzimidazol-2-one, 5.4 parts of 1-(4-methoxyphenyl)-2-(4-piperidinyl)ethanone hydrochloride, 5.3 parts of sodium carbonate, 0.1 parts of potassium iodide and 200 parts of 4-methyl-2-pentanone is distilled azeotropically to dry overnight. After cooling, the precipitated product is filtered off, washed with water and dissolved in trichloromethane. The latter is dried, filtered and evaporated. The residue is crystallized from 2-propanol, yielding 2.9 parts (36.5%) of 1,3-dihydro-1-[2-[4-[2-(4-methoxyphenyl)-2-oxoethyl]-1-piperidinyl]ethyl]-2H-benzimidazol-2-one; mp. 155.9° C.

EXAMPLE XX

To 1 part of a volume of 2 parts of thiophene in 40 parts of ethanol are added 4.1 parts of 1,3-dihydro-1-(3-oxobutyl)-2H-benzimidazol-2-one, 5.2 parts of 1-(4-fluorophenyl)-2-(4-piperidinyl)ethanone hydrochloride, 2 parts of sodium hydrogen carbonate and 160 parts of methanol. The whole is hydrogenated in the Parr-apparatus at 60° C. with 2 parts of palladium-on-charcoal catalyst 10%. After the calculated amount of hydrogen is taken up, the catalyst is filtered off and the filtrate is allowed to crystallize. The product is filtered off and dried, yielding 2.7 parts (33%) of 1-[3-[4-[2-(4-fluorophenyl)-2-oxoethyl]-1-piperidinyl]butyl]-1,3-dihydro-2H-benzimidazol-2-one; mp. 185.4° C.

EXAMPLE XXI

A mixture of 9 parts of 1-[3-[4-[2-(3-chlorophenyl)-2-oxoethyl]-1-piperidinyl]propyl]-1,3-dihydro-3-(1-methylethenyl)-2H-benzimidazol-2-one, 18 parts of a concentrated hydrochloric acid, 80 parts of ethanol and 50 parts of water is stirred for 30 minutes at room temperature. The reaction mixture is evaporated and water is added to the residue. The free base is liberated in the conventional manner with ammonium hydroxide and extracted with trichloromethane. The extract is dried, filtered and evaporated. The oily residue is purified by column-chromatography over silica gel using a mixture of trichloromethane and methanol (90:10 by volume) as eluent. The pure fractions are collected and the eluent is evaporated. The residue is crystallized from 4-methyl-2-pentanone. The product is filtered off and dried, yielding 6.4 parts (78%) of 1-[3-[4-[2-(3-chlorophenyl)-2-oxoethyl]-1-piperidinyl]propyl]-1,3-dihydro-2H-benzimidazol-2-one; mp. 160.3° C.

In a similar manner there are also prepared:

1-[3-[4-[2-(4-bromophenyl)-2-oxoethyl]-1-piperidinyl]propyl]-1,3-dihydro-2H-benzimidazol-2-one; mp. 178.4° C.; and 1,3-dihydro-1-[3-[4-[2-(3-methylphenyl)-2-oxoethyl]-1-piperidinyl]propyl]-2H-benzimidazol-2-one; mp. 132.5° C.

EXAMPLE XXII

To a stirred mixture of 5.5 parts of 1-[2-[4-[2-(4-fluorophenyl)-2-oxoethyl]-1-piperidinyl]ethyl]-1,3-dihydro-2H-benzimidazol-2-one and 80 parts of methanol are added portionwise 0.7 parts of sodium borohydride. Upon completion, stirring is continued for 1 hour at room temperature. Water is added and the whole is evaporated. The residue is taken up in water and the product is extracted with dichloromethane. The extract is dried, filtered and evaporated. The residue is purified by column-chromatography over silica gel using a mixture of trichloromethane and methanol (90:10 by volume) as eluent. The pure fractions are collected and the eluent is evaporated. The oily residue is converted into the hydrochloride salt in 2-propanol and 4-methyl-2-pentanone. The salt is filtered off and dried, yielding 3 parts of 1-[2-[4-[2-(4-fluorophenyl)-2-hydroxyethyl]-1-piperidinyl]ethyl]-1,3-dihydro-2H-benzimidazol-2-one monohydrochloride hemihydrate; mp. 140° C.

Example XXIII

A mixture of 3.1 parts of acetic acid anhydride, 5 parts of 1-[2-[4-[2-(4-fluorophenyl)-2-oxoethyl]-1-piperidinyl]ethyl]-1,3-dihydro-2H-benzimidazol-2-one and 56 parts of methylbenzene is stirred and refluxed for 4 hours. The reaction mixture is cooled and water and ammonium hydroxide are added. Upon stirring, the product is crystallized. It is filtered off, washed with water and dried in vacuo, yielding 2.2 parts (40%) of 1-acetyl-3-[2-[4-[2-(4-fluorophenyl)-2-oxoethyl]-1-piperidinyl]ethyl]-1,3-dihydro-2H-benzimidazol-2-one; mp. 149.2° C.

What is claimed is:

1. A chemical compound selected from the group consisting of a 1,3-dihydro-1-[(1-piperidinyl)alkyl]-2H-benzimidazol-2-one derivative having the formula

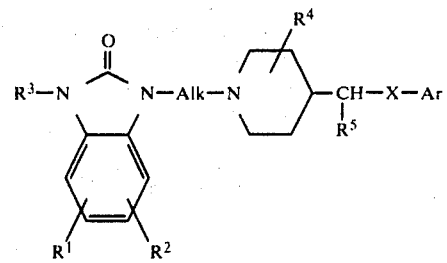

and the pharmaceutically acceptable acid addition salts thereof, wherein:

$R^1$ and $R^2$ are each independently selected from the group consisting of hydrogen, halo, lower alkyl and trifluoromethyl;

$R^3$ is a member selected from the group consisting of hydrogen, lower alkyl and lower alkylcarbonyl;

Alk is a lower alkylene radical;

$R^4$ and $R^5$ are each independently selected from the group consisting of hydrogen and lower alkyl;

X is a member selected from the group consisting of $>C=O$, $>CH-OH$, $>CH-O-C(O)-R_a$, $>CH_2$, $>C(O\text{-lower alkyl})_2$

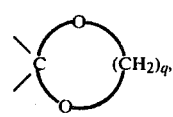

$>C=NOH$ and $>C=N-NH_2$, wherein said $R_a$ is hydrogen or lower alkyl and said q is the integer 2 or 3; and Ar is a member selected from the group consisting of phenyl, substituted phenyl, pyridinyl and thienyl, wherein said substituted phenyl has from 1 to 3 substituents each independently selected from the group consisting of halo, lower alkyl, lower alkoxy, amino, nitro and trifluoromethyl.

2. A chemical compound according to claim 1 wherein $R^4$ is hydrogen.

3. A chemical compound according to claim 1 wherein $R^4$ is hydrogen and X is $>C=O$, $>C(O\text{-lower alkyl})_2$ or

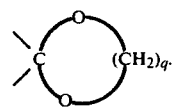

4. A chemical compound according to claim 1 wherein $R^4$ is hydrogen, X is $>C=O$ and Alk represents an 1,2-ethanediyl radical.

5. A chemical compound selected from the group consisting of 1-[2-[4-[2-(4-fluorophenyl)-2-oxoethyl]-1-piperidinyl]ethyl]-1,3-dihydro-2H-benzimidazol-2-one and the pharmaceutically acceptable acid addition salts thereof.

6. An anti-congestive pharmaceutical composition comprising, in admixture with a pharmaceutically-acceptable carrier, an effective anti-congestive amount of the compound of claim 1.

7. An antiemetic pharmaceutical composition comprising, in admixture with a pharmaceutically-acceptable carrier, an effective antiemetic amount of the compound of claim 1.

8. An anti-psychotropic pharmaceutical composition comprising, in admixture with a pharmaceutically-acceptable carrier, an effective psychotropic inhibiting amount of the compound of claim 1.

9. A method of treating congestive diseases of a warm-blooded animal having one of such diseases comprising systemic administration to said animal of an effective anti-congestive amount of the compound of claim 1 in admixture with a pharmaceutically-acceptable carrier.

10. A method of inhibiting emesis in a warm-blooded animal affected by emesis which comprises the systemic administration of an effective antiemetic amount of the compound of claim 1 in admixture with a pharmaceutically-acceptable carrier.

11. A method of treating mental disorders in a warm-blooded animal affected by such disorders which comprises the systemic administration of an effective phychotropic inhibiting amount of the compound of claim 1 in admixture with a pharmaceutically-acceptable carrier.

* * * * *